United States Patent [19]

Forde

[11] Plant 4,388

[45] Feb. 27, 1979

[54] WALNUT TREE

[75] Inventor: Harold I. Forde, Davis, Calif.

[73] Assignee: The Regents of the University of California, Berkeley, Calif.

[21] Appl. No.: 898,597

[22] Filed: Apr. 21, 1978

[51] Int. Cl.[2] ..... A01H 5/03

[52] U.S. Cl. ..... Plt./32

[58] Field of Search ..... Plt./32

*Primary Examiner*—Robert E. Bagwill
*Assistant Examiner*—James R. Feyrer

[57] ABSTRACT

A new and distinct walnut tree being a precocious producer of nuts of nearly elliptical shape with a small point at the apex. The smooth, well filled nuts are well sealed around plump kernels.

2 Drawing Figures

This invention relates to a new and distinct cultivar of walnut tree, botanical classification *Juglans regia.* The original tree grew from a seed from the University of California Walnut Breeding Program, in 1964.

A continuous walnut breeding program has been maintained by the University of California from 1948 to the present time. In 1963, pistillate flowers of the cultivar Pedro were bagged and pollinated with pollen from U.C. Selection 56-224. This selection, U.C. 64-172, grew from one of the resulting seeds, therefore, the parents of this selection are Pedro and U.C. Section 56-224. Pedro was released as a cultivar from the University of California Walnut Breeding Program by E. F. Seer and Harold I. Forde, in 1968. Pedro resulted from crossing Conway Mayette × Payne, in 1952. U.C. 56-224 resulted from the cross Sharkey × Marchetti, in 1955.

Thirty-three seedlings of the cross Pedro × 56-224 were established in the test orchard on the campus of the University of California, Davis. The resulting seedlings were maintained under careful and continuous observation. When such seedlings bore fruit, one which is the instant cultivar evidenced novel and commercially desirable characteristics and was, therefore, selected for asexual reproduction for further testing and possible introduction to the trade.

After its origin, as above, this cultivar named "Chandler," was asexually reproduced by top grafting on trees, of the two common rootstocks. Northern California black walnut *Juglans hindsii* and Paradox *J. hindsii* × *J. regis,* in the University of California (Department of Pomology) experimental orchard. Subsequently, it was also asexually propagated by grafting and budding in test plots in some of the walnut growing areas of California. The trees, leaves, buds and fruit resulting from such reproductions all ran true to the parent trees in every respect.

Figure 1:
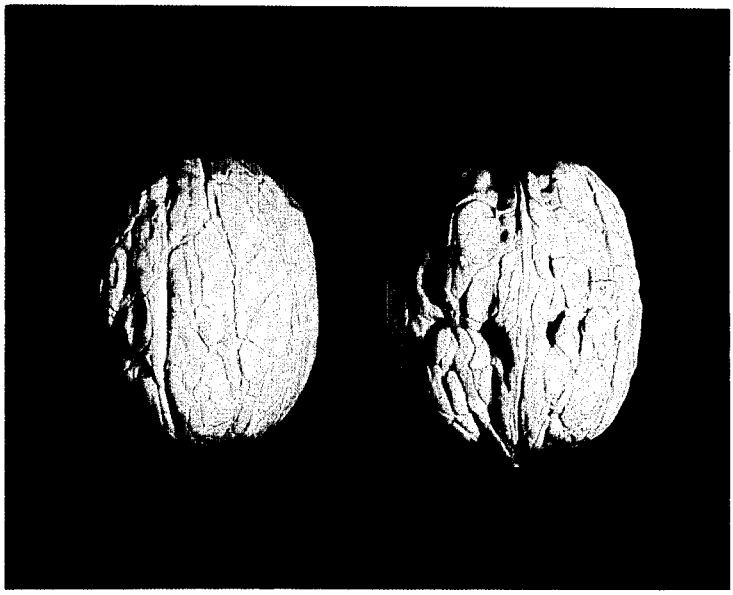
FIG. 1 illustrates two views of nuts in the shell which are typical of the new variety.
Figure 2:
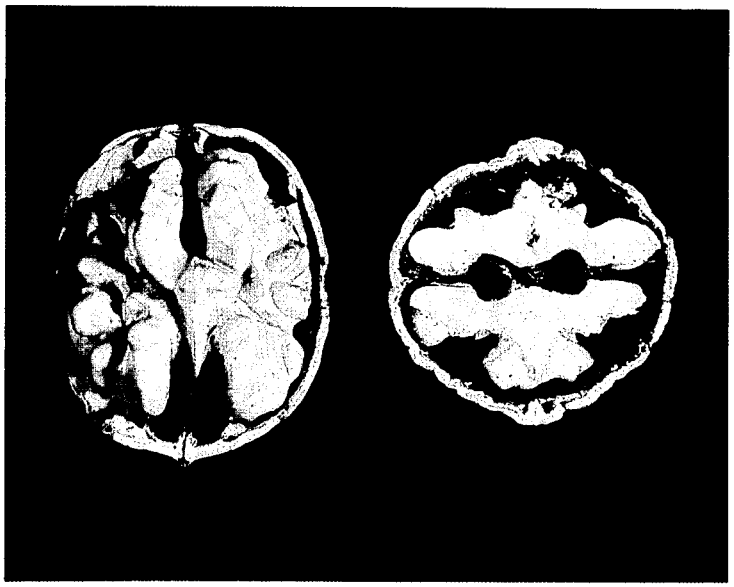
FIG. 2 illustrates the nut in cross section and in longitudinal view with half the shell removed.
Figure 3:
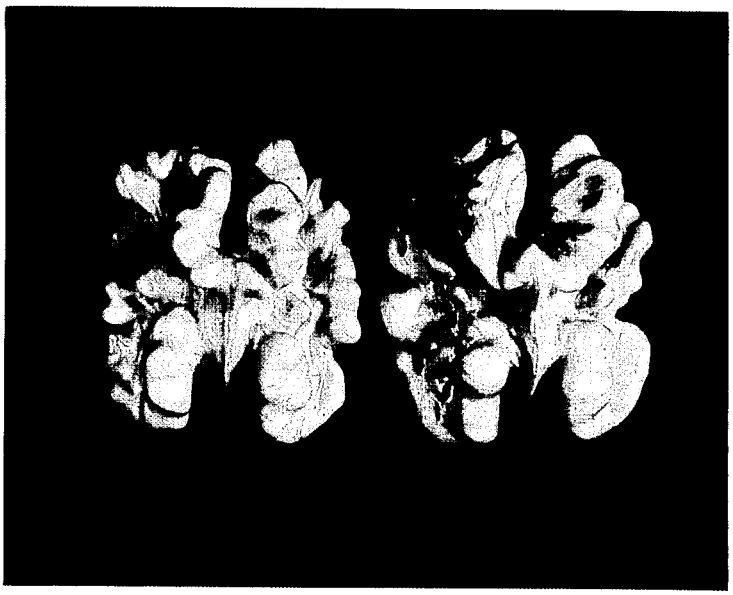
FIG. 3 illustrates kernel halves of the nut of the new variety.

As will be seen from the illustrations, the nuts of this new cultivar are nearly elliptical in shape and have a small point at the apex. The view of the nut showing the suture up shows a slight flattening at both ends. More particularly, as shown in FIG. 1, the nut shell is a medium light color and nearly smooth with small longitudinal grooves. The nuts are well filled, well sealed and have a plump kernel, as indicated by the drawings of FIGS. 2 and 3.

An average well-grown nut of this variety would measure about 41 mm. long with a suture diameter of about 33 mm. and a cheek diameter of about 35 mm. A 500 gr. random sample of 1976 nuts from the plot at Davis contained 38 nuts and had 51 percent light colored kernels, 1 percent amber and no off-grade for a total of 52 percent kernel. Extremely high percent light kernel color has been characteristic of this cultivar every year. The pelicle of the kernel has more gloss than most other walnuts.

Due to very good shell qualities, good shell seal, smoothness, good color and bleach ability, the nuts of this cultivar would be suitable for sale in the shell. Also, due to the moderately high kernel percent and the excellent kernel quality, this cultivar would be highly desirable for shelling and sale of walnuts as kernels.

It will be understood that the new and distinct walnut tree of this variety and its fruit may vary in slight detail due to the climatic and soil conditions under which the cultivar may be grown; the present description being of the cultivar as grown in the University of California orchard at Davis, Calif.

The botanical details of this new and distinct cultivar are as follows:

*Tree.*—Size, medium (similar to Ashley or Vina); vigor, moderately vigorous; growth, semi-upright tree, tends to be a little taller than it is wide, has a round top with slight tendency to conical shape; production, very productive; bearing, early regular bearer.

*Trunk and branches.*—Like most other *J. regia.*

Old bark light gray and smooth, very old bark would probably roughen as it does in other walnuts. New shoots have green bark which turns brown as the season progresses, this is also like other walnuts.

*Leaves.*—Leaves are pinnately compound with 5 to 9 leaflets per leaf. Leaves are green with lower surface being lighter green than the top.

Leaves vary in length from about 20 to 45 cm., averaging about 33 cm. Leaflets vary in length from about 5 to 20 cm., averaging about 15 cm. and in width from about 2 to 10 cm., averaging about 7.0 cm. The basal leaflets are smaller with the terminal leaflet and the leaflets next to it being the largest.

Leaflet shape is elongated ovate. Terminal leaflets are acute at both ends. Lateral leaflets have acute apices and rounded or uneven bases. Uneven bases have blade on one side of the mid-rib 2 to 5 mm. farther from the rachis than it is on the other side.

Leaf texture, smooth; margin, smooth; venation, pinnate.

Start of growth, leafing date, is late mid-season having been 14 to 22 days after Payne, averaging 16 days after Payne. This is practically the same leafing time as Hartley.

*Inflorescence.*—This cultivar is very precocious, young grafted trees having produced pistillate flowers at two years of age and catkins at three years old. About 80 percent of the axillary (lateral) buds produce pistillate flowers.

Full bloom of pistillate flowers has been 34 to 48 days after leafing date of Payne, averaging 39 days after Payne leafing. First pollen shedding has been 17–29 days after Payne leafing with the average being 22 days after Payne. Last pollen shedding has been 28 to 48 days after Payne leafing, with an average of 38 days. Calendar dates in 1976 were pistillate full bloom, April 24, first pollen shed April 6, last pollen shed April 24. The trees have produced many catkins. Most flowering tips have two pistillate flowers, some have three, a few have one and a few have more than three. There is nothing distinctive about the form or color of the male or female flowers as they are similar to most other walnut flowers.

*Harvest.*—Nuts of this cultivar are ready to harvest about 15 days after Payne which is about the same time as Hartley. No other cultivar now in use starting growth and maturing its nuts as late as this cultivar has as high a percentage of axillary buds producing pistillate flowers.

*The fruit.*—The green fruit, before it is ready to harvest is nearly elliptical in longitudinal section and round in cross section. The hull is green with small lenticels and is of about average thickness, the hull is similar in appearance and thickness to the hull of the Payne variety.

The kernel color refers to the standard U.S. Department of Agriculture grading chart.

*The nut and the shell.*—The nuts are nearly elliptical in shape with a small point at the apex. Viewed with the suture up, there is a slight flattening at both ends. The nut shell is a medium light color, nearly smooth and has small longitudinal grooves. As stated, the nuts are well filled, well sealed and have a plump kernel. The average well-grown nut measures about 41 mm. long with a suture diameter of about 33 mm. and a cheek diameter of about 35 mm. A 500 gr. random sample of 1976 nuts contained 38 nuts and had 51 percent light colored kernels, one percent amber colored with no off-grade comprising a total of 52 percent kernel. A distinguishing characteristic of this cultivar in each of its test years demonstrates extremely high percent of light kernel color with the pelicle of the kernel having more gloss than most other walnuts.

I claim:

1. The new and distinct cultivar of walnut tree herein described and illustrated and characterized by its semi-upright growth, moderate vigor, heavy production and mid-season harvest; said variety having its start of growth and its harvest about the same time as Hartley; said variety being further characterized by its production of pistillate flowers on nearly all shoots from terminal buds and on about 80 percent of shoots from axillary buds; said percent being substantially higher than other varieties currently in use and which have the same time of starting growth and nut maturity; said variety being primarily characterized by its nut, a majority of the kernels of which are light colored and glossy; said nut being nearly elliptical in longitudinal section with a small point at the apex and having a nut shell of medium light color, nearly smooth and well filled and sealed.

* * * * *